United States Patent
Vaissiere et al.

(10) Patent No.: US 11,994,488 B2
(45) Date of Patent: May 28, 2024

(54) METHOD OF PREDICTIVE MONITORING OF A VARIABLE OF A MEDIUM AND OF A MEASUREMENT ACCURACY OF A MEASUREMENT DEVICE MEASURING THIS VARIABLE

(71) Applicant: Endress+Hauser Group Services AG, Reinach (CH)

(72) Inventors: Dimitri Vaissiere, Rixheim (FR); Julia Mildner, Gerlingen (DE); André Lemke, Schluchsee (DE)

(73) Assignee: Endress+Hauser Group Services AG, Reinach (CH)

( * ) Notice: Subject to any disclaimer, the term of this patent is extended or adjusted under 35 U.S.C. 154(b) by 58 days.

(21) Appl. No.: 17/530,049

(22) Filed: Nov. 18, 2021

(65) Prior Publication Data
US 2022/0155252 A1 May 19, 2022

(30) Foreign Application Priority Data
Nov. 19, 2020 (DE) ...................... 10 2020 130 623.7

(51) Int. Cl.
*G01N 27/27* (2006.01)
*G01N 27/02* (2006.01)
(Continued)

(52) U.S. Cl.
CPC ............. *G01N 27/27* (2013.01); *G01N 27/02* (2013.01); *G01N 27/302* (2013.01); *G01N 27/333* (2013.01); *G16C 60/00* (2019.02)

(58) Field of Classification Search
CPC ...... G01N 27/27; G01N 27/02; G01N 27/302; G01N 27/333; G01N 27/06; G16C 60/00;
(Continued)

(56) References Cited

U.S. PATENT DOCUMENTS

2019/0323989 A1* 10/2019 Gülfirat ................... H04W 4/38
2020/0204887 A1* 6/2020 Vaissiere ............ G05B 23/0283

FOREIGN PATENT DOCUMENTS

DE 102018217166 A1 9/2019
DE 102018109696 A1 10/2019
(Continued)

OTHER PUBLICATIONS

English translation for KR-101843879B1 (Year: 2018).*
English translation for KR-20170078252A (Year: 2017).*

*Primary Examiner* — Steven L Yeninas
*Assistant Examiner* — Byung Ro Lee
(74) *Attorney, Agent, or Firm* — Kelly J. Smith; Endress+Hauser (USA) Holding, Inc.

(57) ABSTRACT

A method of predictive monitoring of a variable of a medium located in a container of a facility comprises steps of continuously recording data comprising measured values, based on training data determining a classification method capable of identifying data sets that have each been measured during one of the specific operation phases, performing the classification method and based on the data sets identified by the classification method determining a time series of compliancy indicators indicative of a degree of compliancy of at least one property of the characteristic of the measured values to a corresponding reference property of the reference characteristic. Based on the time series at least once determining a time remaining until the degree of compliancy indicated by compliancy indicators will drop below a predetermined minimum degree of compliancy; and providing an output informing about the remaining time.

15 Claims, 4 Drawing Sheets

(51) Int. Cl.
*G01N 27/30* (2006.01)
*G01N 27/333* (2006.01)
*G16C 60/00* (2019.01)

(58) Field of Classification Search
CPC . G05B 23/0283; G05B 23/0221; G01F 23/22; G01F 1/00; G01F 23/24; G01K 13/00
USPC .......................................................... 702/22
See application file for complete search history.

(56) References Cited

FOREIGN PATENT DOCUMENTS

| | | | | |
|---|---|---|---|---|
| EP | 2602680 | B1 | 6/2014 | |
| EP | 3739403 | A1 | 11/2020 | |
| KR | 20170078252 | A * | 7/2017 | .......... G06F 11/3058 |
| KR | 101843879 | B1 * | 3/2018 | ............. G05B 23/02 |

* cited by examiner

METHOD OF PREDICTIVE MONITORING OF A VARIABLE OF A MEDIUM AND OF A MEASUREMENT ACCURACY OF A MEASUREMENT DEVICE MEASURING THIS VARIABLE

CROSS-REFERENCE TO RELATED APPLICATION

The present application is related to and claims the priority benefit of German Patent Application No. 10 2020 130 623.7, filed on Nov. 19, 2020, the entire contents of which are incorporated herein by reference.

TECHNICAL FIELD

The present disclosure concerns a method of predictive monitoring of a variable of a medium located in a container of a facility and of a measurement accuracy of a measurement device measuring this variable during operation of the facility.

BACKGROUND

Measurement devices measuring a variable of a medium located inside a container, like e.g. a tank or a pipe, are used on various types of facilities, like e.g. facilities repeatedly performing a predefined batch process, facilities of industrial plants, like e.g. production plants performing production processes, facilities of chemical plants, facilities of biotechnological plants designed to perform a biotechnological process and laboratory facilities. Measurement devices applied in these applications comprise various types of devices, like e.g. level measurement devices measuring a level of a medium in a container, flow meters measuring a flow of a medium flowing through a pipe, temperature measurement devices measuring a temperature of a medium, pressure measurement devices measuring pressure of a medium, as well as measurement devices, like e.g. amperometric, potentiometric, photometric or spectrometric measurement devices measuring a pH-value of the medium or a concentration of an analyte contained in the medium.

On many facilities, methods of process automation are applied to monitor, to regulate and/or to control operation of the facility based on measurement results provided by measurement instruments measuring parameters required for the respective purpose. These measurement instruments comprise measurement instruments providing measurement results applied to regulate and/or to control the operation of the facility, as well as measurement instruments providing measured values, which are neither applied to regulate nor to control the operation of the facility. In the following, the term measurement instrument is used as generic term for any instruments providing measurement results and the subgroup of measurement instruments providing measured values, which are neither applied to regulate nor to control the operation of the facility are called measurement devices. Examples of measurement devices are e.g. measurement devices applied to monitor the variable measured by them, as well as measurement device applied to confirm that the variable of the medium, like e.g. a medium given by an intermediate or end product produced on the facility, is compliant to a specified requirement. Thus, even though theses measurement devices are neither applied to regulate nor to control the operation of the facility, they nonetheless play a vital part, e.g. in monitoring the operation of the facility and/or in ensuring and/or confirming adherence to predetermined quality standards. Thus, non-compliancy of a measurement device to a specified measurement accuracy may have severe consequences, ranging from impaired production processes, the production and/or the sale of faulty products to potential hazards to people and/or the environment.

Measurement properties, in particular the measurement accuracy, of measurement instruments (including measurement devices) can change over time, e.g. due to aging and/or due to an exposure of the measurement instrument to harsh conditions. To ensure proper operation of measurement instruments they are regularly calibrated and subsequently repaired, adjusted or replaced, in case they are found to no longer comply to the measurement accuracy specified for them during calibration. During calibrations non-compliancy is e.g. determined when a measurement error of the measurement instrument determined during calibration exceeds a maximum permissible error.

Calibrations are not only time and cost intensive but usually also require for the measurement instruments to be removed from the process. As an example, calibration of a pH-measurement instruments comprising a measuring cell closed off by an H+ ion-selective membrane usually requires for the measuring cell to be immersed in a reference solution, like e.g. a buffer solution, such that an outside surface of the membrane is exposed to the reference solution. In some applications, removal of the measurement instrument requires for the operation of the facility to be interrupted. This is especially disadvantageous on facilities, like e.g. facilities performing chemical or biotechnological methods or processes, where high standards of hygiene or even sterility have to be ensured. Even when a calibration does not require an interruption of the operation of the facility, it still causes the problem, that the measurement instrument cannot perform measurements at the facility whilst it is being calibrated.

In consequence, there is a desire to reduce the number of calibrations down to a minimum required to ensure safe operation of the facility and sufficient adherence to quality standards regarding the task performed by the facility, as well as regarding any intermediate or end product produced by performing the task. Unfortunately, due to the multitude of influencing factors affecting the measurement properties of measurement instruments, it is usually not possible to reliably predict a point in time in the future, when the measurement properties of a measurement instrument will have declined so much, that the measurement error of the measurement results provided by the measurement instrument exceeds the maximum permissible error. Thus, to be on the safe side, calibrations are usually performed more often than may be necessary due to the true condition of the measurement instrument.

To improve the situation, calibration time intervals between consecutive calibrations can be optimized. In this context, EP 2 602 680 B1 describes a method of determining an optimized next calibration time, at which a specific measurement instrument requires re-calibration. This next calibration time is determined based on a Monte Carlo simulation performed based on the measurement errors of the measurement instrument determined during at least two previously performed calibrations and probability density functions for determining a measurement error in the respective calibration solely due to an uncertainty inherent to the respective calibration. This method does however require two previously performed calibrations, as well as the uncertainty inherent to the calibrations, which may not always be available.

As an alternative methods enabling verification, calibration and/or adjustment of a measurement instrument measuring a variable to be performed whilst the measurement instrument remains at a measurement site can be performed. Examples are e.g. described in DE 102018109696 A1. These methods are based on reference measurements of the variable performed by an additional measurement instrument. Thus, they cause extra costs and efforts involved in providing the additional measurement instrument, in performing the reference measurements and in ensuring a sufficiently high measurement accuracy of the additional measurement instrument.

Further, a method of operating a measurement instrument measuring a variable at an operating site and of predictive monitoring of a compliancy of at least one characteristic of the measurement instrument to a requirement specified for the measurement instrument is described in European Patent application No. 20168733.2 filed on Apr. 8, 2020. This method is performed based on continuously monitored deviations between measured values determined by the measurement instrument and corresponding reference values. Based on the deviations a remaining time remaining until the deviations will exceed a deviation range defined for the deviations is determined based on a method of time series forecasting. Because this method is performed based on deviations between the monitored variable and corresponding reference values, it can only be applied, when corresponding reference values are available.

SUMMARY

It is an object of the present disclosure to provide a method of predictive monitoring, that enables for both a variable measured by a measurement device and a measurement accuracy of the measurement device to be monitored during operation of the facility and does not require reference measurements of the variable.

To this extent, the present disclosure comprises a method, in particular a computer implemented method, of predictive monitoring of a variable of a medium located in a container of a facility and of a measurement accuracy of a measurement device measuring this variable and providing measured values of this variable during operation of the facility, wherein the facility is operated independently of the measured values and wherein operation of the facility comprises a repeatedly occurring specific operation phase, wherein measured values measured during the specific operation phases exhibit a characteristic distinguishing these measured values from measured values measured during other time periods, and wherein the characteristic is compliant to a reference characteristic when the facility was operating properly and the measurement device was compliant to a specified measurement accuracy during the respective specific operation phase, this method comprising the steps of: installing the measurement device at the facility; during operation of the facility continuously recording data including the measured values measured by the measurement device and their time of measurement; based on training data comprised in this data, that has been recorded during a training time interval, during which the facility was operating properly and during which the measurement device was compliant to the specified measurement accuracy, determining a classification method capable of identifying data sets included in the recorded data, that have each been measured during one of the specific operation phases; performing the classification method and based on the data sets identified by the classification method determining a time series of compliancy indicators indicative of a degree of compliancy of at least one property of the characteristic of the measured values comprised in the data sets to a corresponding reference property of the reference characteristic; based on the time series at least once determining a remaining time remaining until the degree of compliancy indicated by compliancy indicators to be determined based on measured values to be measured during a future occurrence of the specific operation phase will drop below a predetermined minimum degree of compliancy; and providing an output informing about the remaining time.

This method provides the advantages, that it can be performed during operation of the facility, that the measured values measured by the measurement device are available during performance of the method, and that it does not require reference measurements of the variable.

Further, under the precondition, that operation of the facility comprises the repeatedly occurring specific operation phase, wherein measured values measured during the specific operation phases exhibit a sufficiently distinct characteristic, the method provides the advantage, that an identification of the specific operation phase, the determination of the characteristic and the reference characteristic, as well as the determination of the classification method can be performed solely based on the training data without any prior knowledge about the specific operation phase. Thus, neither prior knowledge about the facility and the operation of the facility, nor reference measurements of the variable are required to perform the method.

By requiring the facility to be operated independently of the measured values it is ensured, that the measured values measured by the measurement do not have any direct or indirect effect on the true value of the variable measured. This provides the advantage, that the predictive monitoring not only detects impairments caused by impaired measurement properties of the measurement device but also impairments caused by an impaired operation of the facility affecting the true value of the variable during the specific operation phases.

According to a first refinement, the specific operation phase is predetermined based on information available on the operation of the facility or identified based on the training data; and/or the specific operation phase is: an operation phase occurring during each performance of a predefined batch process, wherein the batch process is repeatedly performed on or by the facility during operation of the facility; an operation phase during which the variable should be equal to a constant; a cleaning phase, wherein said variable of said medium measured by the measurement device during each cleaning phase is the variable of the same cleaning agent applied to clean the container during each cleaning phase, or an empty phase, wherein said variable of said medium measured by the measurement device is the variable of a gas or air comprised in the empty container during each empty phase.

According to a second refinement, the characteristic is determined based on at least one of: the training data and the reference characteristic and/or comprises at least one property of the measured values, the properties comprising at least one of: a value of the measured values, a slope of the measured values, at least one fitted coefficient determinable by fitting the measured values to a function of time and a set of one or more coefficients describing measured values measured during the specific operation phase, a value range in which the measured values occur, a distribution of the measured values, a pattern described by the measured values, at least one property corresponding to a model property of a model, of a deterministic model, of a statistical model or of a hybrid model including deterministic and statistical model components for the measured values measured during the specific operation phase and at least one other property; and the reference characteristic is determined based on the training data and/or includes a reference property for each property of the characteristic, wherein the reference properties are representative of measured values measured during one of the specific operation phases whilst the facility is operating properly and the measurement device is compliant to the specified measurement accuracy, the reference properties including at least one of: a reference value for the measured values, a reference slope, a set of one or more reference coefficients, a reference pattern, a reference distribution, a reference property for at least one model property and at least one other reference property to be expected of measured values measured during the specific operation phases.

According to a third refinement, determining the classification method includes the step of: identifying the specific operation phase, identifying the specific operation phase based on the training data or identifying the specific operation phase based on the training data and potential candidates for the specific operation phase determined based on information available on the operation of the facility; the classification method is performed based on classification criteria determined for the specific operation phase including at least one of: at least one criterium concerning a value or a value range to be expected of measured values measured during the specific operation phase, at least one criterium concerning a pattern described by the measured values to be expected of measured values measured during the specific operation phase, at least one criterium concerning a distribution of the measured values to be expected of measured values measured during the specific operation phase, at least one criterium related to the degree of compliancy of at least one property of the measured values included in the characteristic to the corresponding reference property included in the reference characteristic, at least one criterium related to a model property of a model for the measured values measured during the specific operation phase and at least one other criterium, and/or data sets comprised in the data and fulfilling classification criteria applied to identify the data sets are determined by performing at least one of: a correlation analysis, a pattern recognition method, an auto-correlation analysis and at least one other data analysis method capable of identifying the data sets fulfilling the classification criteria.

According to a fourth refinement, the method further comprises the steps of: identifying at least one group of subsets of the training data, wherein each subset consists of data measured during a subset time interval and wherein subsets belonging to the same group exhibit a degree of similarity larger or equal to a minimum degree of similarity required for the subsets to be considered to be belonging to the same group, wherein identifying the at least one group of subsets is performed by performing at least one of: a correlation analysis, a pattern recognition method, an auto-correlation analysis and at least one other data analysis method capable of identifying subsets representative of the same operation phase; for at least one of the groups applying the subsets comprised in the respective group as reference sets representative of the same operation phase; determining one of the operation phases, for which reference sets have been determined, to be the specific operation phase, determining the characteristic and the reference characteristic based on the reference sets representative of the specific operation phase, and determining at least one of: the classification method and classification criteria for identifying the data sets included in the recorded data based on the reference sets for the specific operation phase.

According to a refinement of the fourth refinement, wherein reference sets for at least two different operation phases have been determined, this method comprising at least one of the steps of: determining the specific operation phase to be one of these different operation phases having a longer duration and/or a higher frequency of occurrence than at least one other operation phase, for which reference sets have been determined, and determining the specific operation phase such, that the reference sets for the specific operation phase have a higher degree of similarity, than the reference sets determined for at least one other operation phase.

According to a fifth refinement, the time series is determined by for each data set identified by the classification method determining one of the compliancy indicators to be equal to a quantitative measure of a degree of similarity of the entire characteristic exhibited by the measured values comprised in the respective data set and the entire reference characteristic; or: the compliancy indicators are indicative of the degree of compliancy of one of the properties of the characteristic to the corresponding reference property and each compliancy indicator of the time series is given by this property of the measured values included in one of the data sets; or the specific operation phase is an operation phase, wherein the variable should be equal to the same constant during each occurrence of this operation phase, the compliancy indicators are given by the measured values comprised in the data sets; and the compliancy indicators drop below the minimum degree of compliancy, when the compliancy indicators, each given by one of the measured values, exceed an indicator value range including a target value for the constant or a reference constant for the constant included in the reference characteristic; or: the specific operation phase is an operation phase, wherein the variable should be equal to the same constant during each occurrence of this operation phase, the compliancy indicators are given by deviations between the measured values included in the data sets and a target value for the constant or a reference constant for the constant included in the reference characteristic; and the compliancy indicators drop below the minimum degree of compliancy, when the compliancy indicators, each given by one of the deviations, exceed a corresponding deviation range.

According to a sixth refinement, the training data is labeled training data comprising the measured values and the respective operation phase, during which they were measured, and at least one of the steps of: identifying the specific operation phase, determining the characteristic, determining the reference characteristic and determining the classification method is performed by performing a method of supervised learning.

According to a seventh refinement, the method additionally comprises the step of determining and discarding at least one of: potentially polluted measured values and potentially polluted measured values given by edge values measured at the beginning and at the end of the specific operation phase comprised in the identified data sets before determining the time series.

According to an eight refinement, the method comprises the step of providing the continuously recorded data to a calculating unit, wherein the calculating unit: is embodied to perform, trained to perform and/or designed to learn and to perform at least one of: identifying the specific operation phase and determining the classification method based on the data provided to it; determines and performs the classification method based on the data provided to it; determines the time series; and/or determines the remaining time.

According to a ninth refinement, the facility is embodied to perform a predetermined task or a predetermined process and/or or to repeatedly perform a predetermined batch process; and/or the measurement device is an electrochemical measurement device measuring a concentration of an analyte contained in the medium or a pH-sensor measuring a pH-value of the medium.

According to a tenth refinement, the measurement device measures at least one parameter; the continuously recorded data includes measured parameter values of the parameter(s) measured and provided by the measurement device and their time of measurement; and at least one of: identifying the specific operation phase, determining the characteristic, determining the reference characteristic, determining the classification method, performing the classification method and determining the time series is performed based on the measured values and the measured parameter values included in the training data.

According to a refinement of the tenth refinement, the at least one parameter include at least one of: at least one parameter measured by a sensor of the measurement device, at least one parameter applied by the measurement device to determine the measured values of the variable; at least one parameter applied by the measurement device to compensate a parameter-dependent measurement error; a temperature measured by a temperature sensor of the measurement device; and an electrode potential of a measuring electrode of the measurement device and/or an electrical impedance of an ion-selective membrane of the measurement device, wherein the measurement device is an electrochemical measurement device measuring a concentration of an analyte contained in the medium or a pH-sensor measuring a pH-value of the medium and includes: a measuring cell closed off by the ion-selective membrane having an inside surface exposed to an electrolyte located inside the measuring cell and an outside surface exposed to the medium and the measuring electrode immersed into the electrolyte.

According to an eleventh refinement, each remaining time is determined by performing a method of time series forecasting or by performing a method of time series forecasting comprising the steps of: for each compliancy indicator comprised in the time series determining a deviation between the respective compliancy indicator and a target value for the degree of compliancy or a target value for the degree of compliancy of 100%, filtering the deviations, based on the deviations and the filtered deviations determining a noise superimposed on the filtered deviations, and at the end of at least one monitoring time interval, during which three or more compliancy indicators comprised in the time series have been determined and none of the compliancy indicator were below the minimum degree of compliancy, determining the remaining time as a remaining time remaining until the deviations will exceed a deviation range, wherein the deviation range is determined based on the minimum degree of compliancy such, that the deviations exceed the deviation range when the degree of compliancy indicated by the compliancy indicators drops below the minimum degree of compliancy, and wherein the remaining time is determined by: for at least two different deviation pairs, each including a first deviation and a second deviation determined based on the filtered deviations included in the monitoring time interval, determining a simulated value of the remaining time by performing a Monte Carlo simulation based on the noise and the respective deviation pair, and determining the remaining time based on, as an average of or as a weighted average of the simulated values determined for each deviation pair.

According to a twelfth refinement, the method comprises the steps of: calibrating the measurement device at or before the point in time at which the degree of compliancy indicated by the compliancy indicators will drop below the minimum degree of compliancy according to the previously determined remaining time; during calibration determining a measurement error of the measurement device; in case the measurement error is smaller than a predetermined threshold performing at least one of: determining an impaired operation of the facility as root cause causing the degree of compliancy to drop below the minimum degree of compliancy, and determining a fault causing the impaired operation and applying a remedy resolving the fault; and in case the measurement error is larger than a predetermined threshold performing at least one of: determining impaired measurement properties of the measurement device as root cause causing the degree of compliancy to drop below the minimum degree of compliancy, and adjusting, repairing or replacing the measurement device, and restarting the method from the beginning by installing the measurement device, which is compliant to the measurement accuracy specified for it.

According to a thirteens refinement, wherein operation of the facility includes a repeatedly occurring additional specific operation phase, wherein measured values measured during the additional specific operation phases exhibit a characteristic distinguishing these measured values from measured values measured during other time periods, and wherein the characteristic is compliant to a reference characteristic when the facility was operating properly and the measurement device was compliant to the specified measurement accuracy during the respective additional specific operation phase, the method comprises the steps of: based on the training data determining an additional classification method capable of identifying additional data sets of measured values included in the recorded data, that have each been measured during one of the additional specific operation phases; performing the additional classification method and based on the measured values included in the additional data sets identified by the additional classification method determining an additional time series of compliancy indicators indicative of a degree of compliancy of at least one property of the characteristic of the measured values included in the additional data sets to a corresponding reference property of the reference characteristic; based on the additional time series at least once determining an additional remaining time remaining until the degree of compliancy indicated by compliancy indicators to be determined based on measured values to be measured during a future occurrence of the additional specific operation phase will drop below a predetermined additional minimum degree of compliancy, and providing an output informing about the additional remaining time.

BRIEF DESCRIPTION OF THE DRAWINGS

The present disclosure and further advantages are explained in more detail using the figures of the drawing.

DETAILED DESCRIPTION

The present disclosure concerns a method, in particular a computer implemented method, of predictive monitoring of a variable of a medium 5 located in a container 1 of a facility and of a measurement accuracy of a measurement device 3 measuring this variable and providing measured values m(ti) of this variable during operation of the facility, wherein the facility is operated independently of the measured values m(ti) and wherein operation of the facility comprises a repeatedly occurring specific operation phase Ps, wherein measured values m(ti) measured during the specific operation phases Ps exhibit a characteristic C distinguishing these measured values m(ti) from measured values measured m(ti) during other time periods, and wherein the characteristic C is compliant to a reference characteristic Cr when the facility was operating properly and the measurement device 3 was compliant to a specified measurement accuracy during the respective specific operation phase Ps.

Figure 1:
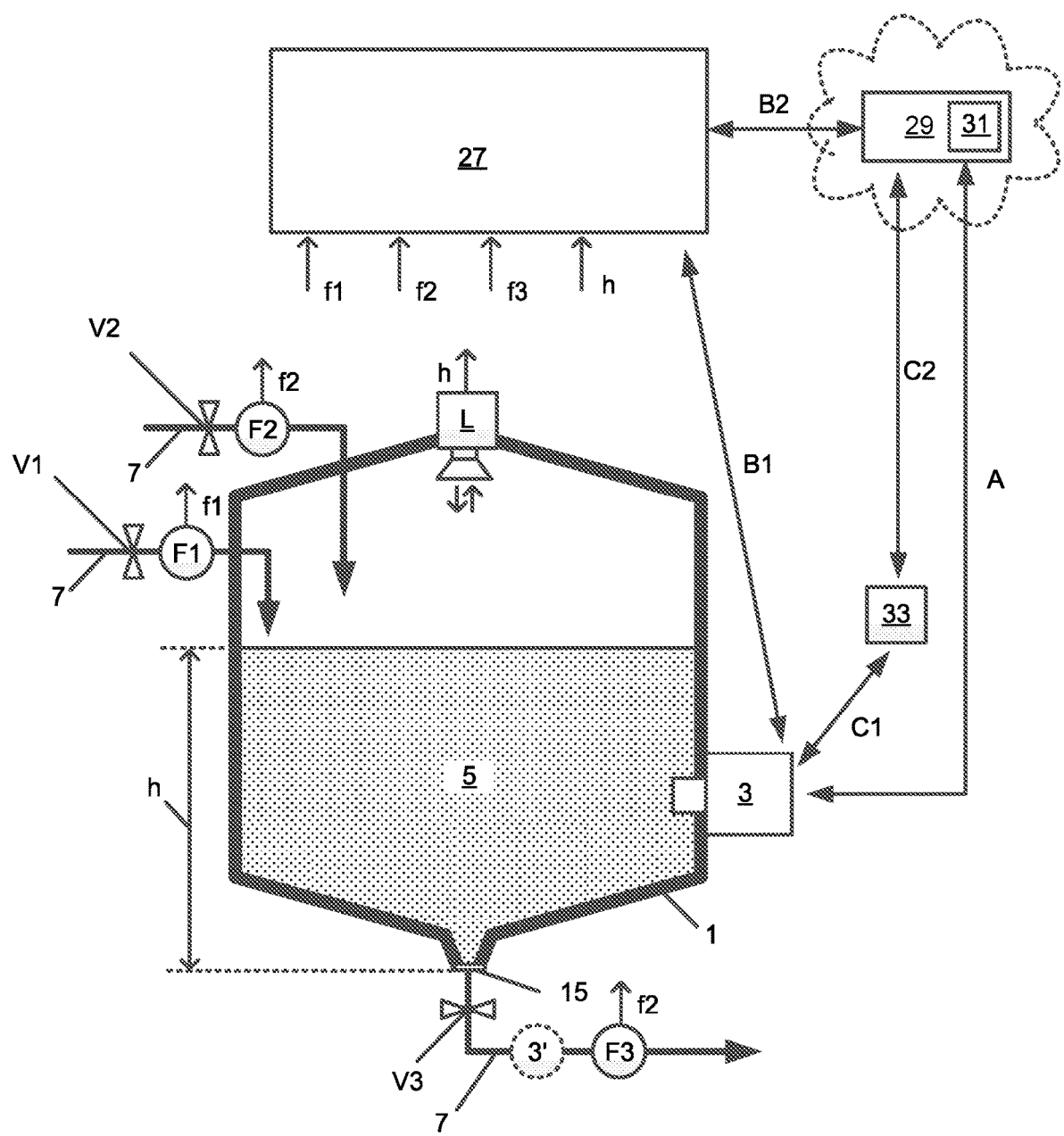
FIG. 1 depicts a facility including a measurement device.

FIG. 1 shows an example of a facility designed to repeatedly perform a predetermined batch process. In this example, the container 1 is a tank, like e.g. a bioreactor, and the measurement device 3 is installed on the container 1 and measures the variable of the medium 5 comprised in the container 1. The present disclosure is not limited to facilities performing batch processes. As an alternative, the facility can be another type of facility, like e.g. a facility designed to perform at least one given task, like e.g. a facility of a production plant performing a production process, a facility of a chemical plant, a facility of a biotechnological plant, or a facility of a laboratory, like e.g. a facility performing laboratory analyses. In addition, the container 1 does not have to be a tank. The method can be applied in the same way, with respect to a measurement device installed on another type of container having an interior containing the medium. Examples are open or closed vessels, as well as pipes including the medium located inside the pipe and/or flowing through the pipe. As an example, the method can e.g. be applied in the same way, with respect to the measurement device 3', indicated by dotted lines in FIG. 1, installed in or on one of the pipes 7 connected to the tank.

Figure 2:
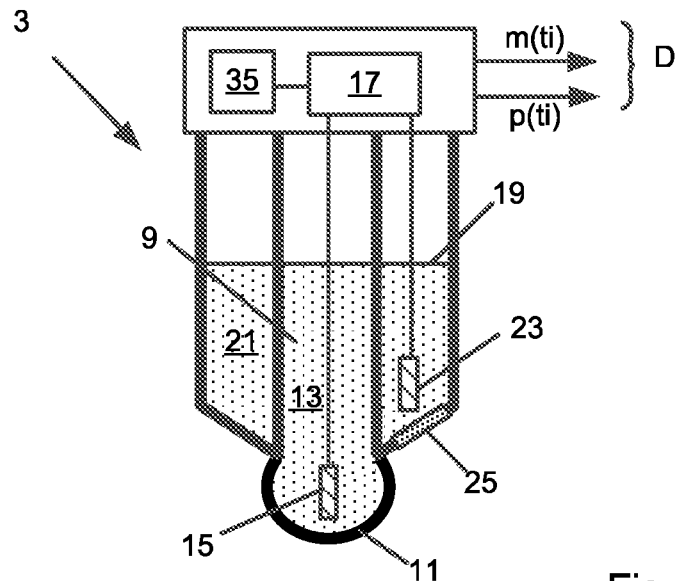
FIG. 2 depicts an example of a measurement device.

The measurement device 3 is e.g. an electrochemical sensor, e.g. a potentiometric sensor measuring an activity or a concentration of an analyte comprised in the medium 5 or a pH-value of the medium 5. An example of an electrochemical sensor, like e.g. a pH-sensor is shown in FIG. 2. This sensor includes a measuring cell 9 closed off by an ion-selective membrane 11, like e.g. H+-ion selective membrane, having an inside surface exposed to an electrolyte 13 located inside the measuring cell 9, like e.g. a pH buffer solution, and an outside surface exposed to the medium 5 surrounding it. Due to the ion-selective interaction of the membrane 11 with the medium 5, an electric potential Uel corresponding to the variable to be measured, like e.g. a pH-value of the medium 5, can be derived via a measuring electrode 15 extending into the electrolyte 13. The measuring electrode 15 is connected to measurement electronics 17 embodied to quantitatively determine the variable based on the electrode potential Uel provided by the measuring electrode 15 or based on a difference between the electrode potential Uel and a reference potential Uref. As an option, the reference potential Uref is e.g. a potential provided by a reference cell 19. In the example shown, the reference cell 19 included an electrolyte 21 located inside the reference cell 19, a reference electrode 23 extending into this electrolyte 21 and a diaphragm 25 permeable to charge carriers. The diaphragm 25 is inserted into a wall section of an outside wall of the reference cell 19 such that an inner surface of the diaphragm 25 is exposed to the electrolyte 21 located inside the reference cell 19 and an outer surface of the diaphragm 25 is exposed to the medium 5 surrounding it. The present disclosure is not limited to pH-sensors. As an alternative the measurement device 3 can e.g. be another type of measurement device and/or a measurement device measuring another variable, like e.g. a pressure or a turbidity, of the medium 5 comprised in the container 1.

As an example operation of the facility shown in FIG. 1 e.g. comprises repeated performances of a batch process, like e.g. a batch process producing a batch of a product, like e.g. a protein or lemonade, comprising a sequence of operation phases. As an example, the sequence e.g. comprises:
  a) an empty phase Pe, during which the container 1 is empty,
  b) a first filling phase Pf1, during which a pre-product is supplied to the container 1 through one of the pipes 7,
  c) a second filling phase Pf2, during which a reactant is supplied to the container 1 through one of the pipes 7,
  d) a reaction phase Pr, during which a reaction is taking place inside the container 1, and
  e) a discharging phase Pd, during which a batch of a product obtained by the reaction is discharged through one of the pipes 7.

As an option, operation of the facility may additionally include a repeatedly performed cleaning phase Pc, during which the container 1 is cleaned with a cleaning agent. The cleaning phases Pc can e.g. be performed in between consecutively performed batch processes, like e.g. after each discharging phase Pd.

As mentioned above, operation of the facility is performed independently of the measured values m(ti) measured by the measurement device 3. This means, that operation of the facility is neither regulated nor controlled based on the measured values m(ti) measured by the measurement device 3 and that the measured values m(ti) are neither applied to regulate nor to control the operation of the facility. This is e.g. the case for measurement devices 3 solely applied to monitor operation of the facility and/or to confirm that the variable of the medium 5 is compliant to a requirement specified for it. By operating the facility independently of the measured values m(ti) it is ensured, that the measured values m(ti) do not have any direct or indirect effect on the true value of the variable measured by the measurement device 3.

As an option, operation of the facility is e.g. monitored, regulated and/or controlled by a super-ordinated unit 27. As an example, the super-ordinated unit 27 is e.g. a unit including or consisting of a system, like e.g. a programmable logical controller, regulating and/or controlling operation of the facility based on measurement results provided by measuring instruments measuring parameters required to regulate and/or to control the operation of the facility. As an example, operation of the facility shown in FIG. 1 is e.g. regulated and/or controlled based on measurement results f1, f2, f3, provided by flow meters F1, F2, F3 installed on the pipes 7 measuring a flow flowing into or out of the container 1 through the respective pipe 7 and/or measurement results h of a level measurement instrument L measuring a level of the medium 5 comprised in the container 1. Regulation and/or control is e.g. performed by adjusting valve settings of valves V1, V2, V3 inserted into the pipes 7 based on these measurement results f1, f2, f3, h. As an alternative other means and/or methods of operating the facility independently of the measured values m(ti) can be applied.

The method comprises the step of installing the measurement device 3 at the facility and of operating the facility. During operation of the facility the variable of the medium 5 is measured by the measurement device 3 and data D including the measured values m(ti) measured and provided by the measurement device 3 and their time of measurement ti is continuously recorded.

Figure 3:
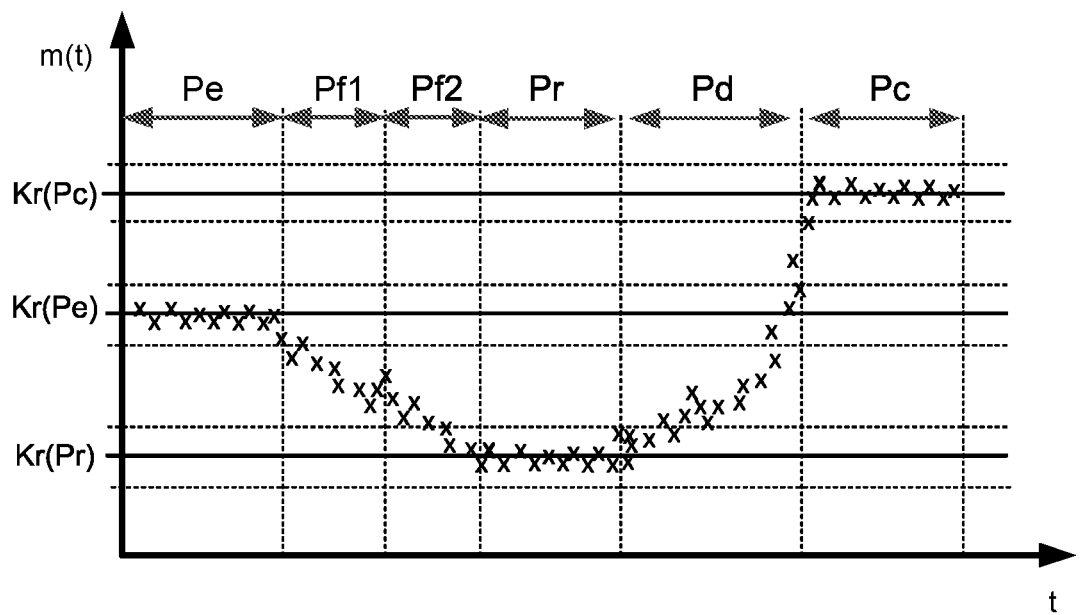
FIG. 3 depicts measured values measured by the measurement device of FIG. 1.

FIG. 3 shows an example of measured values m(ti) measured by the measurement device 3 during a single performance of the batch process described above and a subsequently performed cleaning phase Pc. In this example, the measured values m(ti) are approximately constant during the empty phase Pe, during the reaction phase Pr and during the cleaning phase Pc. Further, they decrease during the first filling phase Pf1 and during the second filling phase Pf2 and increase during the discharging phase Pd.

During operation of the facility, the predictive monitoring is performed based on the continuously recorded data D. As a precondition, the monitoring method requires for the operation of the facility to comprise the repeatedly occurring specific operation phase Ps, wherein measured values m(ti) measured during the specific operation phases Ps exhibit the characteristic C distinguishing the measured values m(ti) measured during the specific operation phases Ps from measured values measured m(ti) during other time periods, and wherein the characteristic C is compliant to the reference characteristic Cr, when the facility was operating properly and the measurement device 3 was compliant to the specified measurement accuracy during the respective specific operation phase Ps.

It depends of on the type of the facility, the task performed by the facility and the variable measured by the measurement device 3, which operation phase repeatedly occurring during operation of the facility produces measured values m(ti) exhibiting a sufficiently distinct characteristic C in a sufficiently reproducible manner and can thus be applied as the specific operation phase Ps in the method described herein. Examples are:
  a) an operation phase occurring during each performance of a repeatedly performed batch process, like e.g. one of the operation phases of the batch process described above;
  b) an operation phase during which the variable should be equal to a constant K, like e.g. the empty phase Pe, the reaction phase Pr or the cleaning phase Pc mentioned above;
  c) a cleaning phase Pc, wherein the variable measured is the variable of the same cleaning agent applied to clean the container 1 during each cleaning phase Pc, and
  d) an empty phase Pe, wherein the variable measured is the variable of the same gas or air comprised in the empty container 1 during each empty phase Pe.

Assuming proper operation of the facility, each one of the repeatedly occurring operation phases will be performed in the same way each time it occurs. Thus, under ideal conditions, the variable should either be equal to the same constant K or be given by the same deterministic function of time or be given by the same statistical pattern during each one of the repeated occurrences of the same operation phase. In consequence, additionally assuming proper operation of the measurement device 3, the measured values m(ti) measured during consecutive occurrences of the same operation phase should be the same within a tolerance accounting for variations due to the operation of the facility, the associated reproducibility of the trueness of the variable to the constant, the function or the pattern and variations accounting for the measurement properties and the limited measurement accuracy of the measurement device 3.

Provided that operation of the facility comprises the repeatedly occurring specific operation phase Ps, wherein the measured values m(ti) measured during these specific operation phase Ps fulfill the requirement mentioned above, this automatically causes each characteristic C of measured values m(ti) measured during one of the specific operation phases Ps whilst the facility was operating properly and the measurement device 3 was compliant to the specified measurement accuracy to be compliant to reference characteristic Cr.

As an example, the characteristic C is e.g. a characteristic including at least one property of the measured values m(ti), like e.g. their values, their slope, a value range in which they occur, their distribution and/or a pattern described by them during the specific operation phase Ps. The at least one property of the measured values m(ti) e.g. comprises at least one property corresponding to a model property of a model for the measured values m(ti) measured during the specific operation phase Ps. Suitable models include deterministic models, like e.g. physical models, for the deterministic behavior of the measured values m(ti), statistical models, like e.g. models for the statistical behavior of the measured values m(ti), as well as hybrid models combining deterministic and statistical model components. Correspondingly, the reference characteristic Cr includes a reference property for each property included in the characteristic C, like e.g. a reference value, a reference slope, a reference value range, a reference pattern, a reference distribution, and/or a reference property for each of the model properties applied, representative of measured values m(ti) measured during one of the specific operation phases Ps whilst the facility was operating properly and the measurement device 3 was compliant to the specified measurement accuracy. Thus, measured values m(ti) measured during one of the specific operation phases Ps, can be distinguished from measured values m(ti) measured during other time periods, based on a degree of compliancy of their characteristic C to the reference characteristic Cr.

To this extent the method comprises a preliminary step of determining a classification method capable of identifying data sets S comprised in the data D, that have each been measured during one of the specific operation phases Ps. The classification method is determined based on training data comprised in the data D, that has been measured during a training time interval TI, during which the facility was operating properly and during which the measurement device 3 was compliant to the measurement accuracy specified for it. As an example, the training time interval TI is e.g. an interval following the installation of the measurement device 3. Compliancy to the specified measurement accuracy is e.g. ensured by requiring for the measurement device 3 to be installed to be a new device or a newly calibrated device compliant to the specified measurement accuracy.

As an option, the determination of the classification method is e.g. performed by a calculating unit 29 embodied to determine the classification method based on the continuously recorded data D provided to it. The calculating unit 29 is e.g. trained to perform or designed to learn the determination of the classification method and to subsequently perform the classification method. In this case, the calculation unit 29 is e.g. embodied, e.g. trained or designed to learn, to determine classification criteria for identifying data sets S comprising measured values m(ti) measured during one of the specific operation phases Ps in the recorded data D based on the training data.

Providing the data D to the calculating unit 29 is e.g. performed by transmitting the data D to a memory 31 associated to the calculating unit 29 and at least temporarily storing the data D in this memory 31. To do so, the measurement device 3 providing the measured values m(ti) and their time of measurement ti can e.g. be connected to and/or communicate with the calculation unit 29 directly, e.g. as illustrated by the arrow A, via the super-ordinated unit 27, e.g. as illustrate by the arrows B1 and B2, and/or via an edge device 33 located in the vicinity of the measurement device 3, e.g. as indicated by the arrows C1, C2. To this extent hard wired or wireless connections and/or communication protocols known in the art, like e.g. LAN, W-LAN, Fieldbus, Profibus, Hart, Bluetooth, Near Field Communication etc. can be applied. As an example, the measurement device 3, the edge device 33 and/or the super-ordinated 27 can be directly or indirectly connected to the calculation unit 29 via the internet, e.g. via a communication network, like e.g. TCP/IP.

The calculation unit 29 is e.g. embodied as a unit including hardware, like e.g. a computer or a computing system, located in the vicinity of the measurement device 3 or at a remote location. As an alternative option cloud computing can be applied. Cloud computing denominates an approach, wherein IT-infrastructure, like hardware, computing power, memory, network capacity and/or software are provided via a network, e.g. via the internet. In that case, the calculation unit 29 is embodied in the cloud.

The classification method can be any method capable of identifying the data sets S in the continuously recorded data D. Determination of the classification method based on the training data is possible, due to the compliancy of the characteristic C exhibited by the measured values m(ti) measured during the specific operation phase Ps to the reference characteristic Cr during proper operation of the facility and of the measurement device 3. Thus, provided that the reference characteristic Cr is sufficiently distinct, the reference characteristic Cr is determinable and/or determined based on the training data. As an option, at least one of the models for the measured values m(ti) mentioned above and the corresponding at least one model property is determinable and/or determined based on the training data. In consequence, the characteristic C is determinable and/or determined based on the reference characteristic Cr and classification criteria enabling the identification of the data sets S are determinable and/or determined based on the training data without any prior knowledge about the characteristic C and the reference characteristic Cr.

As an example, the classification criteria e.g. comprise at least one criterium concerning a value, a slope or a value range to be expected of measured values m(ti) measured during the specific operation phase Ps, at least one criterium concerning the distribution of the measured values m(ti) to be expected of measured values m(ti) measured during the specific operation phase Ps, at least one criterium concerning the pattern described by the measured values m(ti) to be expected of measured values m(ti) measured during the specific operation phase Ps, and/or at least one criterium concerning one of the model properties to be expected of measured values m(ti) measured during the specific operation phase Ps. As an additional or alternative option, the classification criteria e.g. comprise at least one criterium related to the degree of compliancy of at least one property of the measured values m(ti) included in the characteristic C to the corresponding reference property included in the reference characteristic Cr.

As an option, the determination of the characteristic C, the determination of the reference characteristic Cr, the determination of the degree of compliancy of at least one or all properties of the characteristic C of the measured values m(ti) to the corresponding reference properties of the reference characteristic Cr, the determination of classification criteria and/or the identification of the data sets S comprised in the data D, is e.g. determined by applying classification algorithms, like e.g. algorithm applied in support vector machines, in dynamic time warping or neural networks.

The specific operation phase Ps is e.g. a repeatedly occurring operation phase that was predetermined based on information available on the operation of the facility. As alternative option, the specific operation phase Ps is identified based on the training data. In the latter case, as an option, the determination of the classification method e.g. includes the step of identifying the specific operation phase Ps.

When information on the operation of the facility is available, this information can be used to predetermine the specific operation phase Ps or to identify one or more potential candidates that might be suitable to be applied as the specific operation phase Ps and to identify the specific operation phase Ps based on these candidates. As an example, an operation phase, wherein the variable should be equal to the same constant K during each occurrence of the respective operation phase can be predetermined to be the specific operation phase Ps or can be identified as one of the at least one potential candidates for the specific operation phase Ps. In the example shown in FIGS. 1 and 3, suitable candidates are e.g.

the empty phases Pe, wherein the variable should be equal to a constant K(Pe) given by a variable value of the medium 5, namely air or gas comprised in the empty container 1, during each empty phase Pe, the reaction phases Pr, wherein the variable should be equal to a constant K(Pr) given by a variable value of the medium 5, namely the product reacting inside the container 1, during each reaction phase Pr, and the cleaning phases Pc, wherein the variable should be equal to a constant K(Pc) given by a variable value of the medium 5, namely the cleaning agent applied, during each cleaning phase Pc.

In case the variable should be constant during the specific operation phase Ps, the classification criteria e.g. include a criterium requiring for the measured values m(ti) to be stationary.

The present disclosure is however not limited to specific operation phases Ps, during which the variable should be constant.

As an additional or alternative option, when labeled training data including the measured values m(ti) and the respective operation phase, during which they were measured, is available, one of the at least one repeatedly occurring operation phases can be identified as the specific operation phase Ps and the characteristic C, the reference characteristic Cr and the classification method are e.g. determined by performing a method of supervised learning.

As an alternative option, identification of the specific operation phase Ps is e.g. performed without any prior knowledge about the repeatedly occurring operation phases and/or about potentially suitable candidates for the specific operation phase Ps. Thus, the specific operation phase Ps, can even be an operation phase, the owner or user of the facility is unaware of. Regardless of whether candidates have been identified or not, the identification of the specific operation phase Ps and the determination of the classification method are e.g. both performed based on the training data comprised in the data D. This identification can be performed without any prior knowledge about the characteristic C and the reference characteristic Cr associated with the specific operation phase Ps.

As an example, identification of the specific operation phase Ps is e.g. performed by identifying at least one group Gj of subsets of the training data, wherein each subset consists of data measured during a subset time interval and wherein subsets belonging to the same group Gj exhibit a degree of similarity that is larger or equal to a minimum degree of similarity required for the subsets to be considered to be belonging to the same group Gj. Thus, subsets comprised in the same group Gj can be considered to have been measured during the same operation phase and are thus representative of the respective operation phase. Determining subsets belonging to the same group Gj is e.g. performed by performing at least one of: an analysis of the values of the measured values m(ti), a correlation analysis, a pattern recognition method, an autocorrelation analysis, and another data analysis method capable of identifying subsets of sufficiently high similarity.

As an example, based on training data measured during several consecutive performances of the batch process, each followed by the cleaning phase Pc described above based on FIGS. 1 and 3, a maximum of six different groups Gj of subsets, each corresponding to one of the six operation phases Pe, Pf1, Pf2, Pr, Pd, Pc can be determined.

Next, for at least one of the groups Gj the subsets comprised in the respective group Gj that are representative of the same operation phase are identified as reference sets for the respective operation phase.

When reference sets can be and/or are only determined for single operation phase, this operation phase is determined to be the specific operation phase Ps and the characteristic C of the measured values m(ti) measured during this specific operation phase Ps, the reference characteristic Cr and classification criteria, like e.g. classification criteria including at least one of the criteria mentioned above, for identifying the data sets S are determined based on these reference sets.

When reference sets for two or more operation phases have been determined, one of these operation phases is determined to be the specific operation phase Ps and the characteristic C, the reference characteristic Cr and the classification criteria for identifying the data sets S measured during specific operation phases Ps are determined as described above based on the reference sets for this specific operation phase Ps. As an option, one of the operation phases, for which reference sets have been determined, can be arbitrarily selected to be the specific operation phase Ps. As an alternative, the selection is e.g. performed based on a frequency of occurrence and/or a duration of these operation phases. In addition or as an alternative, the selection is preferably performed based on a degree of similarity of the reference sets comprised in the same group Gj. Selecting an operation phase having a higher frequency of occurrence than at least one of the other operation phases, as well as selecting an operation phase having a longer duration than at least one of the other operation phases provides the advantage, that it increases the number and the rate of availability of measured values m(ti) measured during the specific operation phases Ps. Selecting an operation phase, for which reference sets exhibiting a higher degree of similarity have been determined improves the preciseness of the classification criteria and thus improves the capability of the classification method to identify the data sets S.

Due to the fact, that the training data was recorded during proper operation of the facility and of the measurement device 3, each characteristic C determinable based on the measured values m(ti) comprised in one of the reference sets is compliant to the reference characteristic Cr. Thus, the reference characteristic Cr is determinable and/or determined based on the reference sets. Further, classification criteria corresponding to the reference characteristic Cr are determinable and/or determined based on the reference sets.

As an alternative other ways of identifying the specific operation phase Ps, another type of classification method and/or another method of determining the classification method and/or the classification criteria can be used instead. As an example, the calculation unit 29 is e.g. embodied to perform a process of machine learning. In this case the calculation unit 29 learns the classification method based on the training data and subsequently identifies the data sets S comprised in the data D by performing the learned method.

Following the determination of the classification method, the data sets S comprised in the data D are identified by performing this method. As an example, the classification method is e.g. performed by determining limited time intervals, wherein the measured values m(ti) measured during the respective time interval fulfill the classification criteria characteristic for the specific operation phase Ps and by identifying the fractions of the data D measured during these limited time intervals as the data sets S. Determining the measured values m(ti) measured during one of the limited time intervals and fulfilling the classification criteria is e.g. performed by performing at least one of: a correlation analysis, a pattern recognition method, an autocorrelation analysis, and/or another data analysis method capable of identifying the data sets S fulfilling the classification criteria.

Based on the data sets S identified by the classification method, a time series ts of compliancy indicators I indicative of a degree of compliancy of at least one property of the characteristic C of the measured values m(ti) comprised in the respective data sets S to the corresponding reference property of the reference characteristic Cr is determined. This time series ts is continuously extended based on the data D continuously recorded during operation of the facility. Further, it is applied to at least once determine a remaining time RT remaining until the degree of compliancy indicated by compliancy indicators I to be determined based on measured values m(ti) measured during a future occurrence of the specific operation phase Ps will drop below a predetermined minimum degree of compliancy Imin. Determination of each remaining time RT is e.g. performed by performing a method of time series forecasting performed based on the compliancy indicators I comprised in the time series ts.

Each remaining time RT is e.g. determined in form of a point in time tRT in the future at which the compliancy indicator I(tRT) will drop below the minimum degree of compliancy Imin and/or in form of a remaining time interval RTI remaining until this point in time tRT.

The determination of the time series ts is e.g. performed by the calculating unit 29 embodied to determine the time series ts based on the continuously recorded data D provided to it or based on the data sets S provided to it and the at least one property of the reference characteristic Cr determined by or provided to it. The calculating unit 29 is e.g. trained to perform or designed to learn and to perform the determination of the time series ts. In addition, the calculating 29 is e.g. embodied to determine the remaining time RT.

Following the determination of the remaining time RT an output informing about the respective remaining time RT is provided. As an example, the output is e.g. provided in form of an e-mail or a message automatically generated by the calculating unit 29 and dispatched to a predetermined recipient or a predetermined device, like e.g. the super-ordinated unit 27, a computer or a mobile device, like e.g. a cell phone, a tablet or a service tool.

The method according to the present disclosure provides the advantages mentioned above. Individual steps of the method can be implemented in different ways without deviating from the scope of the present disclosure. Several optional embodiments are described in more detail below.

With respect to the determination of the time series ts performed based on the data sets S identified by the classification method, different methods can be applied.

As one option, the time series ts is e.g. determined by for each data set S identified by the classification method determining one of the compliancy indicators I of the time series ts. In this case, the time associated with each of the compliancy indicators I is e.g. a time stamp determined based on the time period during which the measured values m(ti) comprised in the respective data set S were measured, like e.g. a time stamp given by a starting time, an end time or a point in time in the middle of the time period.

As an example, these compliancy indicators I are e.g. each determined to be equal to a quantitative measure of a degree of the similarity of the entire characteristic C exhibited by the measured values m(ti) included in the respective data set S and the entire reference characteristic Cr. This type of compliancy indicator I is suitable, when the reference characteristic Cr only comprises the reference pattern and/or the reference distribution described above. In this case, the compliancy indicators I are e.g. each determined based on a degree of similarity of the pattern described by the measured values m(ti) comprised in the respective data set S to the reference pattern and/or a degree of similarity of the distribution of the measured values m(ti) comprised in the respective data set S to the reference distribution.

When the compliancy indicators I are determined based on the degree of similarity of the respective entire characteristic C to the entire reference characteristic Cr they can e.g. be quantitatively determined in form of a percentage, wherein a target value of a degree of compliancy of 100% is achieved, in the ideal case, that characteristic C and reference characteristic are identical.

Figure 4:
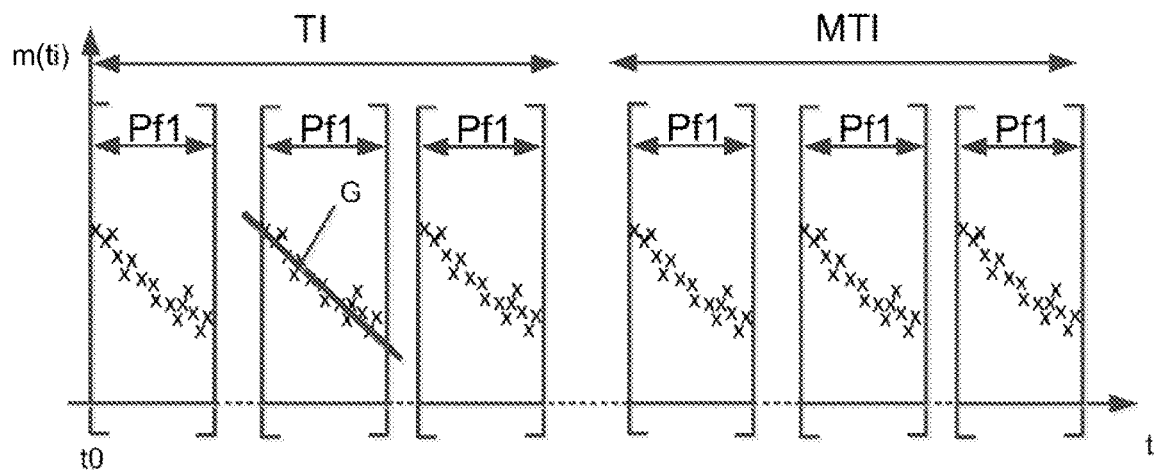
FIG. 4 depicts sets of measured values measured during first filling phases.
Figure 5:
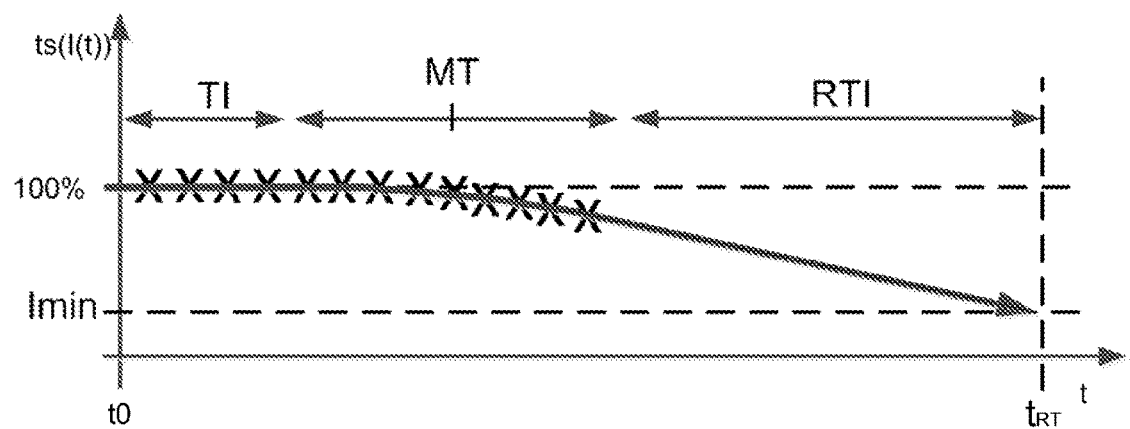
FIG. 5 depicts a time series of compliancy indicators.

FIG. 4 shows an example of sets of measured values m(ti) measured during the specific operation phase Ps. In this example, the first filling phase Pf1 repeatedly occurring in the example shown in FIGS. 1 and 3 is applied as the specific operation phase Ps. Each set includes measured values m(ti) comprised in one of the data sets S, that have been measured during one of the occurrences of the first filling phase Pf1. The extract shown comprises three examples of sets of measured values m(ti), that have been measured during the training time interval TI and three examples of sets of measured values m(ti), that have been measured after the training time interval TI. FIG. 5 shows an example of a corresponding time series ts:=ts(I(t)) of compliancy indicators I, each given by the degree of compliancy of the characteristic C of the measured values m(ti) comprised in one of the data sets S to the reference characteristic Cr. In this example, the compliancy indicators I determined based on data sets S including measured values m(ti) measured after the training time interval TI decrease in time. As illustrated by the arrow in FIG. 5, based on this time series is a method of time series forecasting is e.g. applied to predict the remaining time RT remaining until the compliancy indicator I will drop below the minimum degree of compliancy Imin.

As an alternative option, the compliancy indicators I are e.g. determined based on the degree of compliancy of one or at least two of the properties of the characteristic C to the corresponding reference properties. This option is suitable, when the measured values m(ti) measured during the specific operation phase Ps can be described by a deterministic function f(t) of time t and a set of coefficients. This function f(t) of time t is e.g. determinable and/or determined based on the training data. In this case the characteristic C e.g. comprises a set of fitted coefficients determined by fitting the measured values m(ti) to the function f(t) of time and the reference characteristic Cr comprises the corresponding reference coefficients. In this case, the degree of compliancy is e.g. quantitatively determined based on the deviations between the fitted coefficients and the reference coefficients. As an example, when this type of compliancy indicators I is applied in the example shown in FIG. 4, each compliancy indicator I determined for one of the data sets S is e.g. determined as a deviation between a slope of a straight line G fitted to the measured values m(ti) comprised in the data set S to the corresponding reference slope comprised in the reference characteristic Cr.

When only one property, like e.g. the slope, is applied, the compliancy indicators I are e.g. each given by this property determined based on the respective data sets S. Thus, the time series ts is a time series ts of this property, like e.g. a time series of slopes. In this case, a target value for the degree of compliancy of 100% is achieved, when the properties are identical to the reference property and the compliancy indicators I drop below the minimum degree of compliancy, when the deviation between the property and the reference property exceeds a corresponding deviation range.

When two or more properties are applied, the compliancy indicators I are e.g. each given by a quantitative measure of a deviation between the properties determined based on the respective data sets S and the reference properties. In this case a target value of a degree of compliancy of 100% is achieved, in the ideal case, that the deviation is zero because all properties determined based on the respective data sets S are identical to the reference properties and the compliancy indicators I drop below the minimum degree of compliancy, when the compliancy indicators I given by theses deviations exceed a corresponding deviation range.

As another option, available when the specific operation phase Ps is an operation phase, wherein the variable should be equal to the same constant K during each occurrence of this operation phase, the measured values m(ti) comprised in the data sets S or deviations d(ti): =m(ti)−Kr between these measured values m(ti) and the reference value Kr for the constant K, can be applied as compliancy indicators I. In the first case, the time series ts is a time series ts(m(ti)) of measured values m(ti) measured during the specific operation phases Ps. Here, the compliancy indicators I, each given by one of these measured values m(ti) drop below the minimum degree of compliancy Imin, when the measured values m(ti) exceed an indicator value range ΔK, like e.g. an indicator value range ΔK given ΔK:=[Kr−ΔKr; Kr+ΔKr] including the reference constant Kr. In the second case, the time series ts is a time series ts(d(ti)) of deviations d(ti) and the compliancy indicators I, each given by one of these deviations d(ti) drop below the minimum degree of compliancy Imin, when the deviations d(ti) exceed a corresponding deviation range DR, like e.g. DR:=[−ΔKr;+ΔKr].

Figure 6:
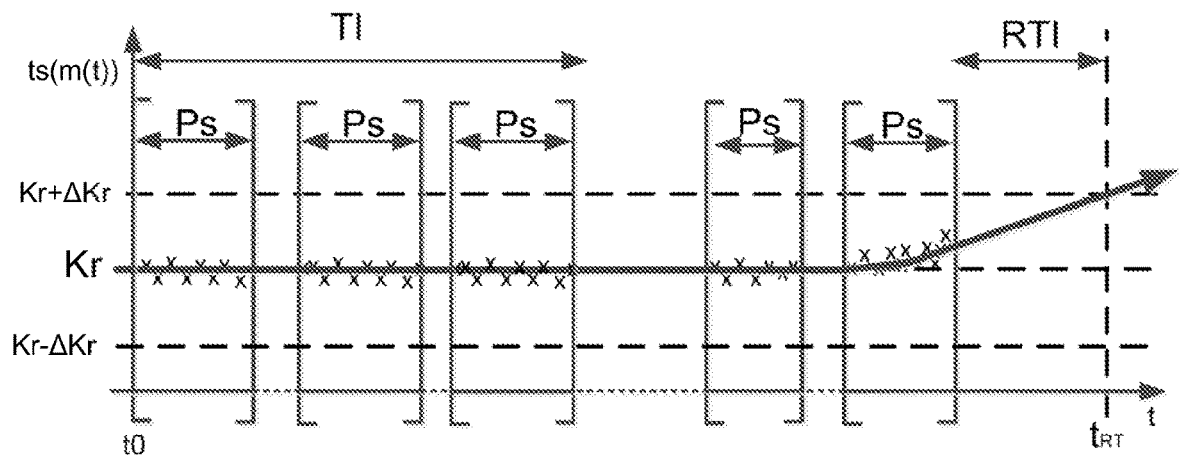
FIG. 6 depicts extracts of a time series of measured values.

FIG. 6 shows an example of an extract of a time series ts of measured values m(ti), wherein each measured value m(ti) is included in one of the data sets S identified by the classification method and measured during one of the specific operation phases Ps. Because the measured the variable should be equal to the constant K during the specific operation phase Ps, the reference constant Kr for the measured values m(ti) comprised in the reference characteristic Cr corresponds to this constant K. As an example, the time series ts is e.g. determined by discarding all data elements comprised the data D apart from the measured values m(ti) comprised in the identified data sets S. The extract shown in FIG. 6 includes three examples of sets of measured values m(ti) measured during the training time interval TI and two examples of sets of measured values m(ti) measured after the training time interval TI. Based on this time series ts a method of time series forecasting can be applied to predict the remaining time RT remaining until the compliancy indicators I given by the measured values m(ti) will drop below the minimum degree of compliancy Imin. As illustrated in FIG. 6, this remaining time RT is e.g. given by the remaining time RT remaining until the measured values m(ti) to be measured during a future occurrences of the specific operation phase Ps will exceed the indicator value range ΔK. In the example shown, the measured values m(ti) measured after the training time interval TI increase in time and will thus exceed an upper limit Kr+ΔKr of the value range ΔK.

In case a target value for the constant K is known, the reference constant Kr can be determined to be equal to the target value. As an alternative, available regardless of whether the target value is known or unknown, the reference constant Kr is e.g. determined based on the measured values m(ti) comprised in the time series ts, that have been measured during the training time interval TI. In this case, the reference constant Kr is e.g. determined to be equal to an average or a mean value of the measured values m(ti) comprised in the time series ts, that have been measured during the training time interval TI.

Regardless of the type of indicator I applied, at least one of the remaining times RT is preferably determined by performing a method of time series forecasting. As an option, at least one of the remaining times RT is e.g. determined by performing a method of time series forecasting described in European Patent application No. 20168733.2 filed on Apr. 8, 2020, incorporated herein by reference. In this case, performance of this method comprises the method steps of:
 a) for each compliancy indicator I comprised in the time series ts determining a deviation d(ti) between the respective compliancy indicator I and a target value for the degree of compliancy, like e.g. a target value of 100%,
 b) filtering the deviations d(ti),
 c) based on the deviations d(ti) and the filtered deviations FD(ti) determining a noise superimposed on the filtered deviations FD(ti), and
 d) at the end of at least one monitoring time interval MTI, during which three or more compliancy indicators I have been determined and none of the compliancy indicators I were below the minimum degree of compliancy Imin, determining the remaining time RT remaining until the deviations d(ti) will exceed a deviation range DR corresponding to the minimum degree of compliancy Imin.

The deviation range DR is determined based on the minimum degree of compliancy Imin such, that the deviations d(ti) exceed the deviation range DR when the degree of compliancy indicated by the compliancy indicators I drops below the minimum degree of compliancy Imin.

When the compliancy indicators I are indicative of a degree of compliancy of a single property of the characteristic C to the corresponding reference properties and the time series ts is a time series ts of this property the deviations d(ti) determined in step a) are given by the deviation between the respective property and the reference property.

When the variable should be constant during each specific operation phase Ps and the time series ts is a time series ts(m(ti)) of measured values m(ti) measured during the specific operation phases Ps, as illustrated in FIG. 6, the deviations d(ti) determined in step a) are given by the deviations d(ti) between the measured values m(ti) and the reference constant Kr. Correspondingly, a target value for the degree of compliancy of 100% is achieved, when the measured values m(ti) are equal to the reference constant Kr and the compliancy indicators I given by the measured values m(ti) drop below the minimum degree of compliancy Imin when the deviations d(ti) exceed the deviation range DR, like e.g. DR:=[−ΔKr;+ΔKr], described above in context with the time series ts(d(ti)) of deviations d(ti).

Figure 7:
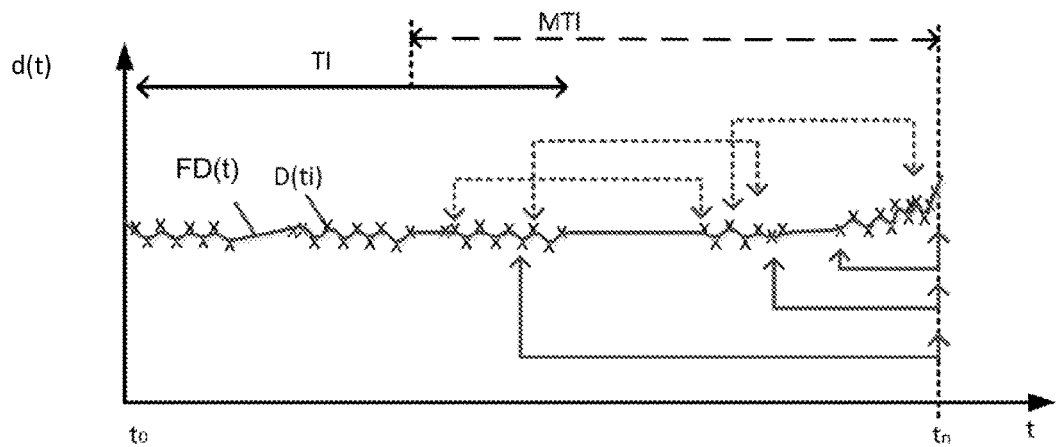
FIG. 7 depicts a time series forecasting method.

This method is illustrated in FIG. 7, wherein the deviations d(ti) between the measured values m(ti) of the time series is shown in FIG. 6 and the reference constant Kr are indicated by crosses, and wherein the filtered deviations FD(ti) are shown in form of a function of time FD(t). As described in European Patent application No. 20168733.2 filed on Apr. 8, 2020, the remaining time RT is determined, by: for at least two different deviation pairs k, each comprising a first deviation $d1k(t1k)$ and a second deviation $d2k(t2k)$ determined based on the filtered deviations FD (t1k), FD (t2k) comprised in the monitoring time interval MTI determining a simulated value SRTk of the remaining time RT by performing a Monte Carlo simulation based on the noise and the respective deviation pair k. As illustrated by the dotted double pointed arrows shown in FIG. 7, the deviation pairs k are e.g. determined such, that the times elapsed between the first and second deviations $d1k(t1k)$, $d2k(t2k)$ of consecutive deviation pairs k form a sliding time window of fixed or variable length sliding along the monitoring time interval MTI. As an alternative, not shown, the deviation pairs k are e.g. determined such, that the second deviation $d2k(t2k)$ of each pair k is given by the last filtered deviation FD(tn) or one of the last filtered deviation FD(ti) comprised in the monitoring time interval MTI.

Figure 8:
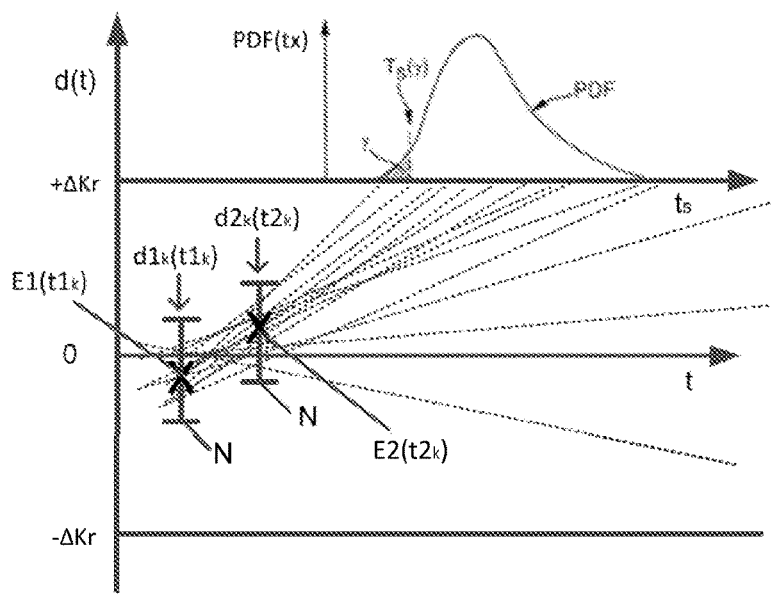
FIG. 8 depicts a determination of a simulated remaining time.

With respect to the Monte Carlo simulations performed to determine the simulated times SRTk, simulation methods known in the art can be applied. FIG. 8 shown an example of a simulation method performed based on one of the deviation pairs k. It comprises a first step of based on the noise, indicated by bars N, the first and the second deviation $d1k(t1k)$, $d2k(t2k)$ and the corresponding times t1k, t2k of this deviation pair k generating a statistically representative number of pairs of first and second random deviations [$E1(t1k):=d1k(t1k)+e1$; $E2(t2k):=d2k(t2k)+e2$], wherein each random deviation E1, E2 is equal to a sum of the respective deviation $d1k(t1k)$, $d2k(t2k)$ of the pair k and a random additive e1, e2 accounting for the noise. In this respect, the random additives e1, e2 are preferably generated according to a probability distribution reflecting the properties of the noise. For each pair of random deviations [E1(t1k); E2(t2k)] a crossing time tx is determined as the time at which a straight line passing through the first random deviation E1(t1k) at the first time t1k and through the second random deviation E2(t2k) at the second time t2k will exceed the deviation range DR. Some examples of the thus determined straight lines are shown as dotted lines in FIG. 8 together with the deviation range DR, represented by the upper and the lower deviation limit −ΔKr, +ΔKr shown in FIG. 8. Based on the crossing times tx a probability density function PDF(tx) of the crossing times tx is determined and the simulated value SRTk is determined based on the probability density function PDF(tx) of the crossing times tx. To this extent, a confidence level γ can be set and the simulated value SRTk can be determined to be equal to the time TS(γ) predicted based on the probability density function PDF(tx) at which the deviations d(ti) will exceed the deviation range DR with a given confidence level γ by solving the following equation for TS(γ):

$$\int_{-\infty}^{TS(\gamma)} PDF(t_x) dt_x = \gamma$$

Following this, the remaining time RT is determined based on the simulated values $SRT_k$ determined for each deviation pair k, e.g. as an average or a weighted average of the simulated values $SRT_k$. In case of a weighted average, the weighing factors applied to the simulated values $SRT_k$ are preferably determined based on the times t1k, t2k corresponding to the first and the second deviation d1k(t1k), d2k(t2k) of the respective deviation pair k, e.g. by:

$$RT = \frac{\sum_{k=1}^{L}(t2_k - t1_k) * SRT_k}{\sum_{k=1}^{L}(t2_k - t1_k)}$$

This method of time series forecasting has the advantage, that each simulated value $SRT_k$ accounts for an average rate of change of the deviations d(ti), that occurred in a time interval elapsed in-between the first and the second deviation d1k(t1k), d2k(t2k) of the respective deviation pair k. Thus, in combination they truly account for the time dependency of the deviations d(ti) in all time intervals covered by the deviation pairs k, even if the time dependency changed during the monitoring time interval MTI. Another advantage is, that the method neither requires for the measured values m(ti) comprised in the time series is to be available at a fixed rate, nor to have been measured at consecutive previously known or predetermined points in time. In addition, performing each of the simulations based on the noise ensures, that the uncertainty inherent to the determination of the deviations d(ti) is accounted for. Since the noise is determined based on the deviations d(ti) and the filtered deviations FD(ti), no additional knowledge about the uncertainty inherent to the determination of the measured values m(ti) and the reference constant Kr is required.

As an alternative, another method of time series forecasting can be applied instead or in combination.

Regardless of the method applied to determine the remaining times RT, as an option, the method can be further improved by following the determination of at least one remaining time RT determining at least one more remaining time RT as described above before the point in time tRT at which the degree of compliancy will drop below the minimum degree of compliancy according to the previously determined remaining time RT. In this case, the output informing about the remaining time RT is preferably updated accordingly every time a new remaining time RT has been determined.

As an additional or alternative option, the method can be further improved by calibrating the measurement device 3 on or before the point in time tRT at which the compliancy indicators I will drop below the minimum degree of compliancy Imin according to the previously determined remaining time RT. During calibration a measurement error of the measurement device 3 determined. This measurement error is then compared to a predetermined threshold. In case the measurement error is larger than the threshold, impaired measurement properties of the measurement device 3 are determined as root cause causing the compliancy indicators I to drop below the minimum degree of compliancy Imin. In this case, the measurement device 3 is preferably adjusted, repaired or replaced and the method is restarted from the beginning by installing the thus obtained measurement device 3, which is compliant to the measurement accuracy specified for it. In case the measurement error is smaller than the threshold, an impaired operation of the facility is determined as root cause, causing the compliancy indicators I to drop below the minimum degree of compliancy Imin. In this case, a fault causing the impaired operation is preferably determined and a corresponding remedy resolving the fault is preferably applied.

As one option, the determination of the time series is can be further refined by following the identification of the data sets S determining and discarding potentially polluted measured values m(ti) comprised in these data set S. As an example the potentially polluted measured values m(ti) e.g. comprise edge values, measured at the beginning and/or at the end of the respective specific operation phase Ps. These edge values may be polluted due to side effects occurring at the transition from the previous operation phase to the respective specific operation phase Ps and at the transition from the respective specific operation phase Ps to the next operation phase. Determination and discarding of the potentially polluted measured values m(ti) is e.g. performed by the calculation unit 29 embodied, e.g. trained or designed to learn, to determine and to discard the potentially polluted measured values m(ti). To this extent, a machine learning method, like e.g. a machine learning method for outlier detection or novelty detection, like e.g. Isolation Forest, Local Outlier Factor, Elliptic Envelope or One Class Support Vector Machine, can be applied. Regardless of how the potentially polluted measured values m(ti) are identified, determining and discarding potentially polluted measured values m(ti) is preferably also applied during the determination of the classification method, e.g. by identifying and discarding potentially polluted measured values comprised to the subsets of the groups Gj determined based on the training data.

As an additional or alternative option, the identification of the specific operation phase Ps, the determination of the characteristic C and/or the reference characteristic Cr, the determination of the classification method, the identification of the data sets S, the performance of the classification method, and/or the determination of the time series is can be further improved by taking into account at least one parameter measured by the measurement device 3 during operation of the facility. As an option, the parameters e.g. comprise at least one parameter measured by a sensor of the measurement device 3, at least one parameter measured and applied by the measurement device 3 to determine the measured values m(ti) and/or to compensate a parameter-dependent measurement error of the measurement device 3. As an example, the parameters e.g. comprise a temperature measured by a temperature sensor 35 of the measurement device 3. When the measurement device 3 is an electrochemical measurement device measuring a measuring a pH-value of the medium or a concentration of an analyte contained in the medium, like e.g. the pH-sensor shown in FIG. 2, the parameters e.g. comprise a parameter given by the electrode potential Uel of the measuring electrode 15 extending into the measuring cell 9 and/or a parameter given by an electrical impedance Z of the membrane 11 closing off the measuring cell 9. In this case, the measurement electronics 17 of the measurement device 3 is e.g. embodied to determine the electrode potential Uel of the electrode 19 connected to the measurement electronics 17 and/or embodied to determine the membrane impedance Z. As an example, the membrane impedance Z is e.g. determined by imposing an alternating voltage on the reference electrode 23 causing the electrode potential Uel to change according to the alternating voltage and the membrane impedance Z. In this case, the membrane impedance Z is e.g. determined based on the dependency of the electrode potential Uel on the alternating voltage and the membrane impedance Z, occurring whilst the alternating voltage is applied to the reference electrode 23.

When at least one parameter is taken into account, the continuously recorded data D additionally comprises parameter values p(ti) of the parameter(s) measured by the measurement device 3 during operation of the facility and their time of measurement ti. In this case, at least one of: the identification of the specific operation phase Ps, the determination of the classification method, the identification of the data sets S, the performance of the classification method, and the determination of the time series ts is performed as described above based on the measured values m(ti) and the measured parameter values p(ti) comprised in this data D. When the measured parameter values p(ti) are applied to determine and/or to perform the classification method, the classification criteria comprise at least one criterium concerning the measured values m(ti) and the measured parameter values p(ti) measured during the specific operation phases Pc. These classification criteria are e.g. determined based on reference sets determined as described above, each comprising the measured values m(ti) and the measured parameter values p(ti). These classification criteria e.g. comprise criteria concerning the values, the value range, the distribution of and/or the pattern described by the measured values m(ti) and/or the measured parameter values p(ti) measured during the specific operation phases Pc. Determining the time series is additionally based on the measured parameter values p(ti) provides the advantage of a more precise and more reliable identification of the data sets S measured during the specific operation phases Ps.

As an option, the measured parameter values p(ti) are e.g. applied with respect to the characteristic C, the reference characteristic Cr and the compliancy indicators I. In this case, the specific operation phase Ps is considered to be a specific operation phase Ps, wherein measured values m(ti) and measured parameter values p(ti) measured during the specific operation phases Ps exhibit the characteristic C distinguishing them from measured values m(ti) and measured parameter values p(ti) measured during other time periods. Just like the characteristic C exhibited by the measured values m(ti), the characteristic C exhibited by the measured values m(ti) and the measured parameter values p(ti) is compliant to the corresponding reference characteristic Cr when the facility is operating properly and the measurement device 3 is compliant to the specified measurement accuracy. Thus, compliancy indicators I indicative of a degree of compliancy of at least one property of the characteristic C of the measured values m(ti) and the measured parameter values p(ti) comprised in the sets S to the corresponding reference property of the reference characteristic Cr, can be applied in the same way as described above with respect to the compliancy indicators I indicative of the degree of compliancy of the at least one property of the characteristic C of the measured values m(ti).

In some applications operation of the facility comprises two or more repeatedly occurring different operation phases, that are suitable to be applied as specific operation phase Ps. As an option, available in these application, at least one additional remaining time RT' can be determined as described above based on at least one additional specific operation phase Ps', wherein measured values m(ti) measured during the additional specific operation phase Ps' exhibit a characteristic C' distinguishing these measured values m(ti) from measured values measured m(ti) during other time periods and wherein the characteristic C' is compliant to a reference characteristic Cr' when the facility is operating properly and the measurement device 3 is compliant to the specified measurement accuracy. In this case, the method comprises the additional steps of: based on the training data determining an additional classification method capable of identifying additional data sets S' comprised in the recorded data D, that have been measured during one of the additional specific operation phases Ps', performing the classification method and based on the additional data sets S' identified by the additional classification method determining an additional time series ts' of compliancy indicators I' indicative of a degree of compliancy of at least one property of the characteristic C' of the measured values m(ti) comprised in the additional data sets S' to the corresponding reference properties of the reference characteristic Cr', based on the additional time series ts' at least once determining an additional remaining time RT' remaining until the degree of compliancy indicated by compliancy indicators I' to be determined based on measured values m(ti) to be measured during a future occurrence of the additional specific operation phase Ps' will drop below a predetermined additional minimum degree of compliancy Imin', and providing an output informing about the additional remaining time RT'.

Performing the method based on the specific operation phase Ps and at least one additional specific operation phase Ps' increases the number and the rate of availability at which measured values m(ti) based on which at least one of: the remaining time RT and the additional remaining time RT' can be determined. This is especially advantageous in application, wherein longer time gabs between consecutive occurrences of the specific operation phase Ps may occur.

The invention claimed is:

1. A method of predictive monitoring of a variable of a medium located in a container of a facility and of a measurement accuracy of a measurement device measuring the variable and providing measured values of the variable during operation of the facility, wherein the facility is configured to repeatedly perform a batch process, a production process, or laboratory analyses, the method comprising the steps of:

installing the measurement device at the facility with the measurement device measuring the variable of the medium and providing measured values of the variable;

operating the facility independently of the measured values of the variable provided by the measurement device, wherein operating the facility includes the facility repeatedly performing specific operation phases of the batch process, the production process, or laboratory analyses, wherein measured values measured during the specific operation phases exhibit a characteristic distinguishing these measured values from measured values measured during other operation phases, and wherein the characteristic corresponds with a reference characteristic when the facility is operating properly and the measurement device corresponds to a specified measurement accuracy during the respective specific operation phase;

during operation of the facility continuously recording data including the measured values measured by the measurement device and their time of measurement;

identifying data sets included in the recorded data that have been measured during the specific operation phases based on training data comprised in the recorded data, which has been recorded during a training time interval during which the facility was operating properly and during which the measurement device operated accorded to the specified measurement accuracy;

monitoring the variable of the medium and the measurement accuracy of the measurement device by:

based on the data sets, comparing compliancy indicators indicative of a degree of compliancy of at least one property of the characteristic of the measured values comprised in the data sets to a corresponding reference property of the reference characteristic;

based on a time series of the determined compliancy indicators at least once determining a remaining time remaining until the degree of compliancy indicated by the compliancy indicators to be determined based on measured values to be measured during a future occurrence of the specific operation phase will drop below a predetermined minimum degree of compliancy;

providing an output informing about the remaining time;

calibrating the measurement device at or before the point in time at which the degree of compliancy indicated by the compliancy indicators will drop below the minimum degree of compliancy according to the previously determined remaining time;

during calibration determining a measurement error of the measurement device;

in case the measurement error is smaller than a predetermined threshold performing at least one of: determining an impaired operation of the facility as root cause causing the degree of compliancy to drop below the minimum degree of compliancy, and determining a fault causing the impaired operation and applying a remedy resolving the fault; and in case the measurement error is larger than a predetermined threshold performing at least one of: determining the impaired measurement properties of the measurement device as root cause causing the degree of compliancy to drop below the minimum degree of compliancy, and adjusting, repairing or replacing the measurement device, which is compliant to the measurement accuracy specified for it.

2. The method according to claim 1, wherein the specific operation phase is predetermined based on information available on the operation of the facility or identified based on the training data; and/or the specific operation phase is:

an operation phase occurring during each performance of a predefined batch process, wherein the batch process is repeatedly performed on or by the facility during operation of the facility;

an operation phase during which the variable should be equal to a constant;

a cleaning phase, wherein said variable of said medium measured by the measurement device during each cleaning phase is the variable of the same cleaning agent applied to clean the container during each cleaning phase, or an empty phase, wherein said variable of said medium measured by the measurement device is the variable of a gas or air comprised in the empty container during each empty phase.

3. The method according to claim 1, wherein:

the characteristic is determined based on at least one of: the training data and the reference characteristic and/or comprises at least one property of the measured values, the properties comprising at least one of: a value of the measured values, a slope of the measured values, at least one fitted coefficient determinable by fitting the measured values to a function of time and a set of one or more coefficients describing measured values measured during the specific operation phase, a value range in which the measured values occur, a distribution of the measured values, a pattern described by the measured values, at least one property corresponding to a model property of a model, of a deterministic model, of a statistical model or of a hybrid model including deterministic and statistical model components for the measured values measured during the specific operation phase and at least one other property; and the reference characteristic is determined based on the training data and/or includes a reference property for each property of the characteristic, wherein the reference properties are representative of measured values measured during one of the specific operation phases whilst the facility is operating properly and the measurement device is compliant to the specified measurement accuracy, the reference properties including at least one of: a reference value for the measured values, a reference slope, a set of one or more reference coefficients, a reference pattern, a reference distribution, a reference property for at least one model property and at least one other reference property to be expected of measured values measured during the specific operation phases.

4. The method according to claim 1, wherein:

determining the classification method includes the step of: identifying the specific operation phase, identifying the specific operation phase based on the training data or identifying the specific operation phase based on the training data and potential candidates for the specific operation phase determined based on information available on the operation of the facility;

the classification method is performed based on classification criteria determined for the specific operation phase including at least one of: at least one criterium concerning a value or a value range to be expected of measured values measured during the specific operation phase, at least one criterium concerning a pattern described by the measured values to be expected of measured values measured during the specific operation phase, at least one criterium concerning a distribution of the measured values to be expected of measured values measured during the specific operation phase, at least one criterium related to the degree of compliancy of at least one property of the measured values included in the characteristic to the corresponding reference property included in the reference characteristic, at least one criterium related to a model property of a model for the measured values measured during the specific operation phase and at least one other criterium, and/or data sets comprised in the data and fulfilling classification criteria applied to identify the data sets are determined by performing at least one of: a correlation analysis, a pattern recognition method, an autocorrelation analysis and at least one other data analysis method capable of identifying the data sets fulfilling the classification criteria.

5. The method according to claim 1, comprising the steps of:

identifying at least one group of subsets of the training data, wherein each subset consists of data measured during a subset time interval and wherein subsets belonging to the same group exhibit a degree of similarity larger or equal to a minimum degree of similarity required for the subsets to be considered to be belonging to the same group, wherein identifying the at least one group of subsets is performed by performing at least one of: a correlation analysis, a pattern recognition method, an autocorrelation analysis and at least one other data analysis method capable of identifying subsets representative of the same operation phase;

for at least one of the groups applying the subsets comprised in the respective group as reference sets representative of the same operation phase;

determining one of the operation phases, for which reference sets have been determined, to be the specific operation phase, determining the characteristic and the reference characteristic based on the reference sets representative of the specific operation phase, and determining at least one of: the classification method and classification criteria for identifying the data sets included in the recorded data based on the reference sets for the specific operation phase.

6. The method according to claim 5, wherein reference sets for at least two different operation phases have been determined, this method comprising at least one of the steps of:

determining the specific operation phase to be one of these different operation phases having a longer duration and/or a higher frequency of occurrence than at least one other operation phase, for which reference sets have been determined, and determining the specific operation phase such, that the reference sets for the specific operation phase have a higher degree of similarity, than the reference sets determined for at least one other operation phase.

7. The method according to claim 1, wherein:

the time series is determined by for each data set identified by the classification method determining one of the compliancy indicators to be equal to a quantitative measure of a degree of similarity of the entire characteristic exhibited by the measured values comprised in the respective data set and the entire reference characteristic;

or wherein: the compliancy indicators are indicative of the degree of compliancy of one of the properties of the characteristic to the corresponding reference property and each compliancy indicator of the time series is given by this property of the measured values included in one of the data sets, or wherein: the specific operation phase is an operation phase, wherein the variable should be equal to the same constant during each occurrence of this operation phase; the compliancy indicators are given by the measured values comprised in the data sets; and the compliancy indicators drop below the minimum degree of compliancy, when the compliancy indicators, each given by one of the measured values, exceed an indicator value range including a target value for the constant or a reference constant for the constant included in the reference characteristic;

or wherein: the specific operation phase is an operation phase, wherein the variable should be equal to the same constant during each occurrence of this operation phase, the compliancy indicators are given by deviations between the measured values included in the data sets and a target value for the constant or a reference constant for the constant included in the reference characteristic; and the compliancy indicators drop below the minimum degree of compliancy, when the compliancy indicators, each given by one of the deviations, exceed a corresponding deviation range.

8. The method according to claim 1, wherein:

the training data is labeled training data comprising the measured values and the respective operation phase, during which they were measured, and at least one of the steps of: identifying the specific operation phase, determining the characteristic, determining the reference characteristic and determining the classification method is performed by performing a method of supervised learning.

9. The method according to claim 1, additionally comprising the step of determining and discarding at least one of: potentially polluted measured values and potentially polluted measured values given by edge values measured at the beginning and at the end of the specific operation phase comprised in the identified data sets before determining the time series.

10. The method according to claim 1, comprising the step of providing the continuously recorded data to a calculating unit, wherein the calculating unit:

is embodied to perform, trained to perform and/or designed to learn and to perform at least one of: identifying the specific operation phase and determining the classification method based on the data provided to it;

determines and performs the classification method based on the data provided to it;

determines the time series; and/or determines the remaining time.

11. The method according to claim 1, wherein:

the facility is embodied to perform a predetermined task or a predetermined process and/or or to repeatedly perform a predetermined batch process; and/or the measurement device is an electrochemical measurement device measuring a concentration of an analyte contained in the medium or a pH-sensor measuring a pH-value of the medium.

12. The method according to claim 1, wherein:

the measurement device measures at least one parameter;

the continuously recorded data includes measured parameter values of the parameter measured and provided by the measurement device and their time of measurement; and at least one of: identifying the specific operation phase, determining the characteristic determining the reference characteristic, determining the classification method, performing the classification method and determining the time series is performed based on the measured values and the measured parameter values included in the training data.

13. The method according to claim 12, wherein the at least one parameter include at least one of:
- at least one parameter measured by a sensor of the measurement device,
- at least one parameter applied by the measurement device to determine the measured values of the variable;
- at least one parameter applied by the measurement device to compensate a parameter-dependent measurement error;
- a temperature measured by a temperature sensor of the measurement device; and
- an electrode potential of a measuring electrode of the measurement device and/or an electrical impedance of an ion-selective membrane of the measurement device, wherein the measurement device is an electrochemical measurement device measuring a concentration of an analyte contained in the medium or a pH-sensor measuring a pH-value of the medium and includes: a measuring cell closed off by the ion-selective membrane having an inside surface exposed to an electrolyte located inside the measuring cell and an outside surface exposed to the medium and the measuring electrode immersed into the electrolyte.

14. The method according to claim 1, wherein each remaining time is determined by performing a method of time series forecasting or by performing a method of time series forecasting comprising the steps of:
- for each compliancy indicator comprised in the time series determining a deviation between the respective compliancy indicator and a target value for the degree of compliancy or a target value for the degree of compliancy of 100%,
- filtering the deviations,
- based on the deviations and the filtered deviations determining a noise superimposed on the filtered deviations, and
- at the end of at least one monitoring time interval, during which three or more compliancy indicators comprised in the time series have been determined and none of the compliancy indicator were below the minimum degree of compliancy, determining the remaining time as a remaining time remaining until the deviations will exceed a deviation range,
- wherein the deviation range is determined based on the minimum degree of compliancy such, that the deviations exceed the deviation range when the degree of compliancy indicated by the compliancy indicators drops below the minimum degree of compliancy, and
- wherein the remaining time is determined by:
  - for at least two different deviation pairs, each including a first deviation and a second deviation determined based on the filtered deviations included in the monitoring time interval, determining a simulated value of the remaining time by performing a Monte Carlo simulation based on the noise and the respective deviation pair, and
  - determining the remaining time based on, as an average of or as a weighted average of the simulated values determined for each deviation pair.

15. The method according to claim 1, wherein operation of the facility includes a repeatedly occurring additional specific operation phase, wherein measured values measured during the additional specific operation phases exhibit a characteristic distinguishing these measured values from measured values measured during other time periods, and wherein the characteristic is compliant to a reference characteristic when the facility was operating properly and the measurement device was compliant to the specified measurement accuracy during the respective additional specific operation phase, this method comprising the steps of:
- based on the training data determining an additional classification method capable of identifying additional data sets of measured values included in the recorded data, that have each been measured during one of the additional specific operation phases;
- performing the additional classification method and based on the measured values included in the additional data sets identified by the additional classification method determining an additional time series of compliancy indicators indicative of a degree of compliancy of at least one property of the characteristic of the measured values included in the additional data sets to a corresponding reference property of the reference characteristic;
- based on the additional time series at least once determining an additional remaining time remaining until the degree of compliancy indicated by compliancy indicators to be determined based on measured values to be measured during a future occurrence of the additional specific operation phase will drop below a predetermined additional minimum degree of compliancy, and
- providing an output informing about the additional remaining time.

* * * * *